(12) United States Patent
Riley et al.

(10) Patent No.: US 9,150,464 B2
(45) Date of Patent: Oct. 6, 2015

(54) METHODS AND APPARATUS FOR TREATING A HYDROCARBON STREAM

(71) Applicant: UOP LLC, Des Plaines, IL (US)

(72) Inventors: Mark G. Riley, Hinsdale, IL (US); Wugeng Liang, Elgin, IL (US); Deng-Yang Jan, Elk Grove Village, IL (US); Adam Gross, Glencoe, IL (US)

(73) Assignee: UOP LLC, Des Plaines, IL (US)

( * ) Notice: Subject to any disclaimer, the term of this patent is extended or adjusted under 35 U.S.C. 154(b) by 234 days.

(21) Appl. No.: 13/904,797

(22) Filed: May 29, 2013

(65) Prior Publication Data

US 2013/0324774 A1 Dec. 5, 2013

Related U.S. Application Data

(60) Provisional application No. 61/653,727, filed on May 31, 2012.

(51) Int. Cl.
| | |
|---|---|
| C07C 7/12 | (2006.01) |
| C07C 7/13 | (2006.01) |
| C07C 7/20 | (2006.01) |
| C07C 5/327 | (2006.01) |
| C07C 2/66 | (2006.01) |
| C07C 2/64 | (2006.01) |

(52) U.S. Cl.
CPC . *C07C 2/64* (2013.01); *C07C 5/327* (2013.01); *C07C 7/12* (2013.01)

(58) Field of Classification Search
USPC ........ 585/823, 804, 806, 807, 808, 441, 323, 585/467
See application file for complete search history.

(56) References Cited

U.S. PATENT DOCUMENTS

| 4,185,040 | A | 1/1980 | Ward |
|---|---|---|---|
| 4,774,377 | A | 9/1988 | Barger |
| 4,846,962 | A | 7/1989 | Yao |
| 4,891,458 | A | 1/1990 | Innes |
| 5,030,786 | A | 7/1991 | Shamshoum |
| 5,220,099 | A | 6/1993 | Schreiner |
| 6,019,887 | A | 2/2000 | Ramirez de Agudelo |
| 6,107,535 | A | 8/2000 | Rossini |
| 6,297,417 | B1 | 10/2001 | Samson |
| 6,756,030 | B1 | 6/2004 | Rohde et al. |
| 7,091,390 | B2 | 8/2006 | Jan |
| 7,205,448 | B2 | 4/2007 | Gajda |
| 7,744,828 | B2 | 6/2010 | Schmidt |
| 8,546,630 | B2 | 10/2013 | Jan |
| 8,546,631 | B2 | 10/2013 | Jan |
| 8,546,632 | B2 | 10/2013 | Jan |
| 2009/0326291 | A1* | 12/2009 | Jan et al. .................... 585/270 |
| 2013/0323133 | A1 | 12/2013 | Liang |
| 2013/0323134 | A1 | 12/2013 | Riley |
| 2013/0324773 | A1 | 12/2013 | Liang |

FOREIGN PATENT DOCUMENTS

| WO | 0035836 A1 | 6/2000 |
|---|---|---|
| WO | 0107383 A1 | 2/2001 |

* cited by examiner

*Primary Examiner* — Thuan D Dang (57) ABSTRACT

Disclosed is a method for removing water, nitrogen compounds, and unsaturated aliphatic compounds from a hydrocarbon feed stream by passing the hydrocarbon feed stream through a water removal zone, a nitrogen removal zone, and an unsaturated aliphatic compound removal zone. By on aspect, the method includes removing water from the hydrocarbon feed stream, contacting the feed stream with a nitrogen selective adsorbent, and contacting the feed stream with an unsaturated aliphatic compound removal material.

8 Claims, 3 Drawing Sheets

METHODS AND APPARATUS FOR TREATING A HYDROCARBON STREAM

CROSS REFERENCE TO RELATED APPLICATION

This application claims priority to U.S. Application No. 61/653,727 which was filed on May 31, 2012.

FIELD OF THE INVENTION

This invention relates to methods and apparatus for treating a hydrocarbon stream. More particularly, this invention relates to methods and apparatus for treating a hydrocarbon stream including an aromatic compound to remove water, nitrogen compounds, and unsaturated aliphatic compounds from the stream.

BACKGROUND OF THE INVENTION

The alkylation or transalkylation of benzene with a C2 to C20 olefin alkylating agent or a polyaklyl aromatic hydrocarbon transalkylating agent is one of the primary sources for the production of alkylbenzenes. For example, ethylbenzene is often produced by the alkylation of benzene with ethylene. Ethylbenzene may subsequently be used as a precursor for making styrene by the dehydrogenation of the ethylbenzene. Often, the ethylbenzene and styrene production facilities are integrated in an ethylbenzene-styrene complex so that after the ethylbenzene is produced it is sent to a downstream styrene plant that converts the ethylbenzene into styrene through dehydrogenation. Styrene may in turn be used to produce polystyrene, a widely used plastic, or other products.

In an alkylbenzene production plant, benzene is fed along with a C2 to C20 olefin alkylating agent or polyalkylaromatic hydrocarbon transalkylating agent to an alkylation or transalkylation reactor. Typically, benzene is fed along with ethylene into an alkylation zone, including an alkylation reactor, where alkylation of the benzene and ethylene over an alkylation catalyst forms ethylbenzene. The ethylbenzene product stream typically includes other components as well, such as diethylbenzene. The stream may next be sent to a separation zone where the ethylbenzene is separated from other components in the stream to form a purified ethylbenzene stream.

In an ethylbenzene-styrene complex, the ethylbenzene is next sent to a downstream styrene plant or section of the complex for conversion of the ethylbenzene to styrene. According to one current process, the ethylbenzene is sent to a dehydrogenation reactor within the styrene plant, where a dehydrogenation reaction occurs to form a mixed stream of styrene, benzene, and ethylbenzene. The mixed stream is sent to an ethylbenzene-styrene splitter forming separate ethylbenzene and styrene streams. An inhibitor is typically added to the ethylbenzene-styrene splitter to restrict polymerization of the styrene and corrosion within the splitter. In many instances, the inhibitors include nitrogen compounds. The ethylbenzene stream may be sent to an ethylbenzene recycle column where an ethylbenzene recycle stream is separated from benzene and toluene. The ethylbenzene may be recycled back to the dehydrogenation reactor or reactors in order to produce additional styrene. The benzene and toluene are typically sent to a benzene-toluene splitter where the streams are separated and may be sold.

Catalysts for aromatic conversion processes generally comprise zeolitic molecular sieves. Examples include, zeolite beta (U.S. Pat. No. 4,891,458); zeolite Y, zeolite omega and zeolite beta (U.S. Pat. No. 5,030,786); X, Y, L, B, ZSM-5, MCM-22, MCM-36, MCM-49, MCM-56 and Omega crystal types (U.S. Pat. No. 4,185,040); X, Y, ultrastable Y, L, Omega, and mordenite zeolites (U.S. Pat. No. 4,774,377); and UZM-8 zeolites (U.S. Pat. Nos. 6,756,030 and 7,091,390). It is known in the art that the benzene stream generated by the styrene zone includes contaminants, such as nitrogen, unsaturated aliphatic compounds, and water such that it has been undesirable to recycle the stream back to the alkylation reactor to produce additional ethylbenzene. These contaminants, even at ppm and ppb levels, can cumulatively act to poison the aromatic conversion catalysts, such as aromatic alkylation catalysts and significantly shorten their useful life. More particularly, nitrogen compounds in the benzene stream, as well as water and dienes or other unsaturated aliphatic compounds, are known to deactivate the alkylation or transalkylation catalyst in the alkylation zone and/or transalkylation zone adding additional expense in having to change out or regenerate the catalyst. In addition, due to the contaminants in this stream, the sale of this benzene stream to third parties is generally below the typical market value of benzene A variety of guard beds having clay, zeolite, or resin adsorbents to remove one or more types of nitrogen compounds and/or other contaminants from an aromatic hydrocarbon stream upstream of an aromatic conversion process are known in the art. Examples include: U.S. Pat. Nos. 7,205,448; 7,744,828; 6,297,417; 5,220,099; WO 00/35836; WO 01/07383; U.S. Pat. Nos. 4,846,962; 6,019,887; and 6,107,535. An acidic molecular sieve H—Y has been utilized to adsorb the nitrogen compounds from the stream.

It was previously identified that unsaturated aliphatic hydrocarbons such as olefinic compounds, and particularly dienes, can shorten the effective life of adsorbents, e.g. nitrogen adsorptive adsorbents, used in the nitrogen removal guard beds that are applied to various process streams, including aromatic hydrocarbon feeds upstream of an aromatic conversion process such as alkylation. These unsaturated aliphatic, e.g. olefinic, compounds are present in aromatic process streams contaminated with nitrogen compounds, including the benzene streams generated in styrene process separation plants and other streams requiring removal of the nitrogen compounds prior to being contacted with a catalyst or other material susceptible to nitrogen poisoning. More particularly, because dienes are typically present at concentrations at least one order of magnitude greater than the concentration of nitrogen compounds in the stream, and compete for adsorbent sites in previous guard beds, they can greatly reduce the capacity of the guard bed. Thus, attempts to simply increase the size of the nitrogen guard bed have been largely ineffective.

Recent attempts, as described in U.S. patent application Ser. Nos. 13/314,796; 13/314,749; and 13/314,842 have focused on removing the olefinic compounds, and in particular dienes such as butadiene or isoprene from a benzene feed stream or a benzene stream exiting the styrene plant prior to directing the stream through a nitrogen compound removal guard bed. In this manner, a large portion of the dienes can be removed from the stream prior to contacting the guard bed catalyst with the stream to restrict the dienes from contacting the guard bed and poisoning the nitrogen adsorbent. With this in mind, these applications propose contacting the benzene or other aromatic stream with adsorbents and/or catalysts including clay, acidic molecular sieves, and/or activated carbon in order to remove at least a portion of the dienes or other C2 to C20 olefin alkylating agent or a poly-alkyl aromatic hydrocarbon transalkylating agents present in a recycle or a fresh feed stream prior to contacting the stream with the nitrogen removal adsorbent to restrict these components from shortening the life of the nitrogen guard bed.

It is also generally known that feed streams to alkylation reactors in an ethylbenzene plant may include water. Particularly, a recycle benzene stream from a styrene monomer production zone has been found to include relatively large amounts of water. Without being bound by theory, it is believed that the H—Y acidic molecular sieve typically used to adsorb the nitrogen compounds from the stream favors water to a much greater extent than nitrogen compounds. In this regard, where water is present in greater amounts than the nitrogen compounds, significant adsorbent capacity is taken up by water, shortening the cycle length or life of the adsorbent. Further, it is believed that certain adsorbents, such as the H—Y acidic molecular sieve used for nitrogen removal may catalyze the polymerization of dienes. This can lead to the blockage of accessible surface area of the adsorbent and coke formation where the adsorbent is regenerated by carbon burn further degrading the effectiveness and useful life of the adsorbent for removing nitrogen components from the stream.

Increases in crude oil prices have created renewed interest in utilizing available streams for recycle in petrochemical processes. Thus, it is desirable to identify ways to utilize feeds and recycle streams in an effective and economical manner for use in aromatic conversion processes while avoiding the problems associated with the presence of the contaminants in the feeds as discussed above.

DETAILED DESCRIPTION OF THE INVENTION

Hydrocarbon conversion processes, such alkylation and/or transalkylation of a benzene feed stream to form ethylbenzene and the dehydrogenation of the ethylbenzene stream to form a styrene monomer stream are well known. Various aspects provided herein provide methods and apparatus for treating a hydrocarbon feed stream, including, for example, a recycle feed stream, to hydrocarbon conversion processes, wherein water, one or more nitrogen compounds, and one or more unsaturated aliphatic hydrocarbon compounds are removed from the hydrocarbon feed stream. The hydrocarbon feed stream includes an aromatic compound, water, a nitrogen compound, and an unsaturated aliphatic compound. The treated hydrocarbon feed stream has a lower water, nitrogen compound, and unsaturated aliphatic hydrocarbon content relative to the hydrocarbon feed stream.

In accordance with an aspect, the aromatic hydrocarbon compound may be selected from the group consisting of benzene, toluene, and naphthalene and substituted derivatives thereof, with benzene and its derivatives being preferred aromatic compounds. The aromatic compound may have one or more of the substituents selected from the group consisting of alkyl groups having from 1 to about 20 carbon atoms, hydroxyl groups, and alkoxy groups whose alkyl group also contains from 1 up to 20 carbon atoms. Where the substituent is an alkyl or alkoxy group, a phenyl group can also be substituted on the alkyl chain.

Although unsubstituted and monosubstituted benzenes, toluenes, and naphthalenes, are most often used, polysubstituted aromatics also may be employed. Examples of suitable alkylatable aromatic compounds in addition to those cited above may include anthracene, phenanthrene, biphenyl, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, and so forth. Sources of benzene, toluene, xylene, and or other feed aromatics include product streams from naphtha reforming units, aromatic extraction units, recycle streams from styrene monomer production units, and petrochemical complexes for the producing para-xylene and other aromatics. However, the hydrocarbon feed stream includes at least one aromatic hydrocarbon compounds. According to one example, the concentration of the aromatic compound in the hydrocarbon feed stream ranges from about 5 wt % to about 99.9 wt % of the hydrocarbon feed. By another example, the hydrocarbon feed stream comprises between about 50 wt % and about 99.9 wt % aromatics, and may comprise between about 90 wt % and about 99.9 wt % aromatics.

By one aspect, the hydrocarbon feed stream nitrogen compound may include one or more organic nitrogen compounds. Organic nitrogen compounds typically include a larger proportion of basic nitrogen compounds such as indoles, pyridines, quinolines, diethanol amine (DEA), morpholines including N-formyl-morpholine (NFM) and N-methyl-pyrrolidone (NMP). Organic nitrogen compounds may also include weakly basic nitriles, such as acetonitrile, propionitrile, and acrylonitrile. Specific examples of nitrogen compounds that may be found in the hydrocarbon feed stream include, but are not limited to, nitriles, acetonitrile, and propionitrile.

According to one aspect, the nitrogen compound in the hydrocarbon feed stream may result from adding an inhibitor or a retardant in an upstream process or downstream process where a process stream is recycled back upstream. For ease of explanation, inhibitors and retardants will collectively be referred to as "inhibitors" from here forward. Adding various nitrogen compound containing inhibitors to a stream during certain processes has been found to inhibit polymerization of a component in the stream and/or reduce corrosion of equipment within a processing unit. For example, as illustrated in FIG. 3, which is addressed again further below, an inhibitor may be added to a styrene monomer production zone 205 of an ethylbenzene-styrene complex in order to inhibit polymerization of a styrene monomer within a styrene stream during separation of a styrene product from other components in the styrene stream, in for example, separation zone 255. The inhibitor may also act to reduce corrosion within the vessels used to carry out these processes. In this example, when a benzene stream is recycled from the styrene monomer production zone 205 to provide at least a portion of a hydrocarbon feed stream comprising benzene, the recycle benzene stream may contain residual nitrogen compounds from the upstream addition of the inhibitor. The hydrocarbon feed stream nitrogen compound may be in the same or a different form than the inhibitor nitrogen compound, due to, for example, a reaction or conversion of the inhibitor nitrogen compound.

Chemical compositions of proprietary inhibitors in commercial use are not widely known, however, certain typical characteristics of such inhibitors are generally understood. U.S. Pat. No. 7,276,636, which is incorporated herein by reference, provides a description of the use of inhibitors, general characteristics of inhibitors, and examples of inhibitors that may be used in commercial processes in Col. 3, line 41 through col. 4, line 65. These inhibitors, as well as others, may introduce the nitrogen compounds present in the hydrocarbon feed stream. Some specific, non-limiting examples of nitrogen compounds that may be found in inhibitors include dinitrophenols, 2-sec-butyl-4,6-dinitrophenol, dialkylhydroxylamines, and nitroxides as well as those described in U.S. Pat. No. 7,276,636.

In one example, the hydrocarbon feed stream has a nitrogen component content ranging from about 1 ppm-wt to about 10 ppm-wt. In another example, the concentration of organic nitrogen compounds in the hydrocarbon feed ranges from about 30 ppb-wt (parts per billion by weight) to about 1 mole % of the hydrocarbon feed; the concentration of organic nitrogen compounds may range from about 30 ppb-wt to about 100 ppm-wt (parts per million by weight) of the hydrocarbon feed. In yet another example, the concentration of weakly basic organic nitrogen compounds such as nitriles in the hydrocarbon feed ranges from about 100 ppb-wt to about 100 ppm-wt of the hydrocarbon feed.

According to one aspect, the hydrocarbon feed stream comprises one or more unsaturated aliphatic compounds, including unsaturated cyclic hydrocarbons and straight and branched chain olefinic hydrocarbons (olefins) having one or more double bonds. Thus, as used herein the terms "olefins" and "olefinic hydrocarbons" include diolefin compounds. In an example, the unsaturated aliphatic compound is an olefin compound, and the unsaturated aliphatic compound may be a diolefin compound. In another example, the unsaturated aliphatic compound is one or more diolefin compounds having four, five, or six carbon atoms per molecule, i.e. the unsaturated aliphatic compound may be selected from the group of diolefins consisting of C4-C6 acyclic and cyclic diolefins, and mixtures thereof. In yet another example, the diolefin compound is selected from the group consisting of butadienes, pentadienes, methylbutadienes, hexadienes, methylpentadienes, dimethylbutadienes, acetylenes, cyclopentadiene, alkylcyclopentadiene, cyclohexadiene and mixtures thereof.

In an example, the concentration of diolefin compounds in the hydrocarbon feed ranges from about 30 ppb-wt to about 3000 ppm-wt of the hydrocarbon feed; and the concentration of diolefin compounds may range from about 50 ppb-wt to about 2000 ppm-wt of the hydrocarbon feed. The hydrocarbon feed stream may comprise other olefins such as monoolefins. Typically, the overall concentration of all olefins in the hydrocarbon feed stream will be no more than 1.0 wt-% olefins.

In accordance with one aspect, the hydrocarbon feed stream contains water. In an example, the concentration of water in the hydrocarbon feed ranges from about 10 to about 10,000 ppm-wt of the hydrocarbon feed. In accordance with another example, the concentration of water in the hydrocarbon feed ranges from about 10 to about 1,000 ppm-wt. The hydrocarbon feed stream may also contain oxygenates in addition to water such as, for example, alcohols and ketones that may be removed with the water components from the hydrocarbon feed stream.

In an example, the aromatic compound comprises benzene, the nitrogen compound comprises an organic nitrogen compound, and the unsaturated aliphatic compound comprises an olefin compound. In another example, the aromatic compound comprises benzene, the nitrogen compound comprises an organic nitrogen compound, and the unsaturated aliphatic compound comprises an olefin compound having four to six carbon atoms per molecule. In another example, the aromatic compound comprises benzene, the nitrogen compound comprises an organic nitrogen compound, and the unsaturated aliphatic compound comprises a diolefin compound.

Figure 1:
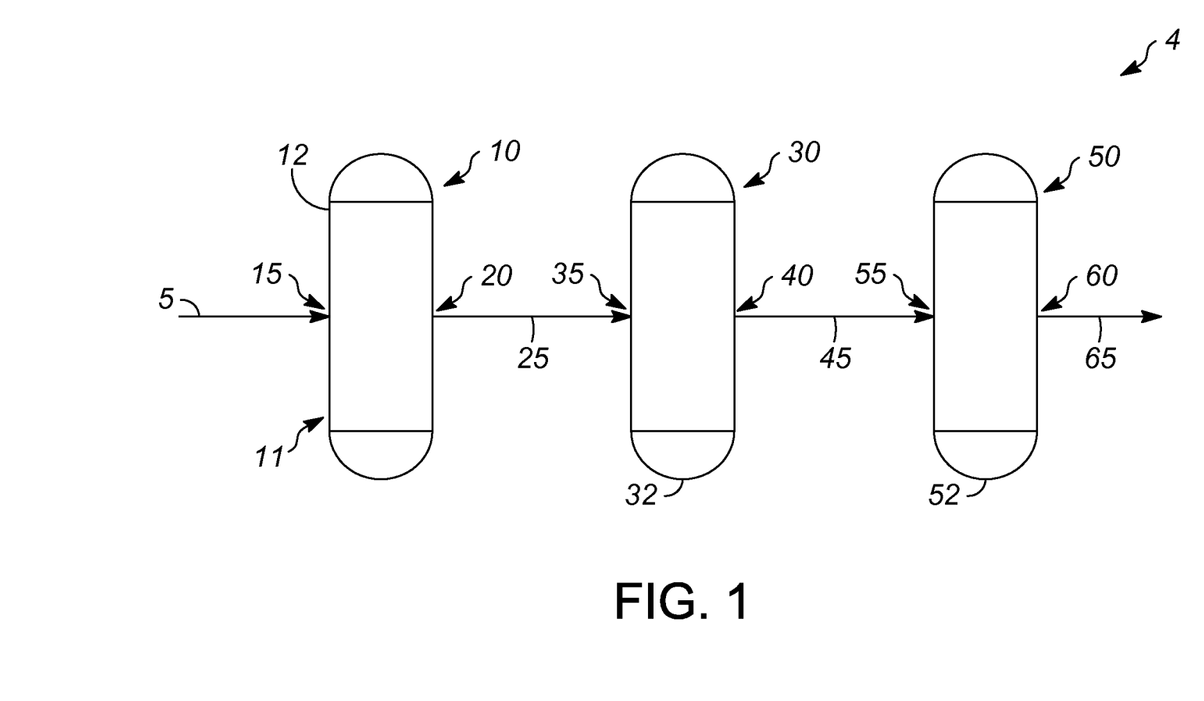
FIG. 1 is a flow diagram of a hydrocarbon feed stream treatment zone in accordance with various embodiments.

Apparatus 2 and processes for treating a hydrocarbon feed stream in accordance with various aspects are provided. Referring to FIG. 1, an apparatus includes a feed stream treatment zone 4 for removing one or more compounds from the feed stream. By one aspect, a hydrocarbon feed stream is provided via line or conduit 5 to a water removal zone 10. The water removal zone includes an inlet 15 in fluid communication with the line 5 for receiving the hydrocarbon feed stream and an outlet 20. The water removal zone removes at least a portion of the water from the hydrocarbon feed stream to provide a reduced water content feed stream. By one aspect, the water removal zone 10 includes a water selective adsorbent that preferentially adsorbs water over one or more other components in the hydrocarbon feed stream that contacts the hydrocarbon feed stream as it flows through the water removal zone 10 to remove at least a portion of the water from the hydrocarbon feed stream. The reduced water content hydrocarbon feed stream having a lower concentration of water relative to the feed stream entering the inlet 15 of the water removal zone, exits through the outlet 20 of the water removal zone into a line 25 in fluid communication with the outlet 20.

By one aspect, the feed stream treatment zone 4 also includes a nitrogen removal zone 30, having a nitrogen removal zone inlet 35 and a nitrogen removal zone outlet 40. The reduced water feed stream is provided to the nitrogen removal zone 30 via the line 25, which provides fluid communication between the water removal zone outlet 20 and the nitrogen removal zone inlet 35. The nitrogen removal zone 30 removes a nitrogen compound from the feed stream to provide a reduced nitrogen feed stream that has a lower nitrogen concentration than the reduced water feed stream entering the nitrogen removal zone 30 via the inlet 35. By one aspect, the nitrogen removal zone 30 includes a nitrogen selective adsorbent that contacts the feed stream and preferentially adsorbs nitrogen over one or more other components in the feed stream for removing the nitrogen compound from the feed stream. A reduced nitrogen feed stream exits the nitrogen removal zone 30 via the outlet 40.

The feed stream treatment zone 4 further includes an unsaturated aliphatic compound removal zone 50 having an unsaturated aliphatic compound removal zone inlet 55 and an unsaturated aliphatic compound removal zone outlet 60. The feed to the aliphatic compound removal zone 50, which has a reduced concentration of both water and one or more nitrogen compounds, is provided to the unsaturated aliphatic compound removal zone 50 via the line 45, which provides fluid communication between the nitrogen removal zone outlet 40 and the unsaturated aliphatic compound removal zone inlet 55. The unsaturated aliphatic compound removal zone 50 removes at least one unsaturated aliphatic compound from the feed stream to provide a reduced unsaturated aliphatic compound feed stream that has a lower concentration of the one or more unsaturated aliphatic compounds than the feed stream entering the unsaturated aliphatic removal zone 50 via the inlet 55. By one aspect, the unsaturated aliphatic compound removal zone includes an unsaturated aliphatic compound adsorbent that preferentially adsorbs the unsaturated aliphatic compound over one or more other components in the feed stream.

By one aspect, the feed stream treatment zone 4 includes all three of the water removal zone 10, the nitrogen removal zone 30, and the unsaturated aliphatic compound treatment zone 50. According to one aspect, the water removal zone 10, the nitrogen removal zone 30, and the unsaturated aliphatic compound treatment zone 50 are provided in series, such that the hydrocarbon feed stream is treated by sequentially passing the hydrocarbon feed stream through the water removal zone 10, the nitrogen removal zone 30, and the unsaturated aliphatic compound treatment zone 50. By another aspect, the hydrocarbon feed stream is sequentially contacted by a water selective adsorbent to remove water from the stream; a nitrogen selective adsorbent to remove nitrogen from the stream, and a unsaturated aliphatic compound adsorbent to remove an unsaturated aliphatic compound from the stream.

Turning to more of the particulars, the water removal zone 10 removes at least a portion of the water from the feed stream. The water removal zone 10 may include a water selective adsorbent that selectively adsorbs water over one or more other components in the feed stream. It should be understood, however, that the water selective adsorbent may also adsorb other components in the feed stream, such as, for example, one or more nitrogen compounds from the feed stream. Further, in accordance with other aspects, other components may be provided in the water removal zone for removing at least a portion of the water from the feed stream. Alternatively, in accordance with other aspects, other apparatus and methods may be provided for removing at least a portion of the water from the hydrocarbon feed stream in the water removal zone 10. For example, trays may be provided for drying the hydrocarbon feed stream as is known in the art. A drier may also be used to remove a portion of the water in the water removal zone 10.

The water may be removed from the hydrocarbon stream by various mechanisms such as adsorption, reaction, and reactive adsorption with the adsorbent. By one aspect, a water selective molecular sieve preferentially adsorbs water over an aromatic compound in the hydrocarbon feed stream. By another aspect, the water selective molecular sieve preferentially adsorbs water over one or more nitrogen compounds and one or more unsaturated aliphatic compounds in the hydrocarbon stream. In one approach, the water selective molecular sieve includes a zeolite material. In one example, the zeolite material may include Zeolite A, Zeolite X, Zeolite Y or mixture of thereof. Examples of specific zeolites that may be used include Zeolites 3A, 4A, 5A and 13X. Zeolites 3A and 4A are preferred as they will not adsorb large amounts of nitrogen compounds, unsaturated aliphatic compounds, benzene or other aromatic hydrocarbons in the feed.

By one aspect, the water selective adsorbent may include a zeolite with a pore diameter that is large enough to adsorb water molecules, but small enough to restrict adsorption of most of the nitrogen compounds and/or unsaturated aliphatic compounds from the stream. Pore diameter refers to the average pore diameter of the adsorbent as measured by gas adsorption methods, including N2 adsorption, and is provided in units of Angstroms. Dubinin-Astakhov or Dubinin-Radushkevich equations may then be used to estimate micropore volume and surface area, from which average pore diameter can be calculated. In one example, the water selective adsorbent may include a zeolite with a pore diameter of between about 2 Å and about 8 Å. By another example, the water selective adsorbent may include a zeolite with a pore diameter of between about 2.5 Å and about 6 Å. In yet another example, the water selective adsorbent may include a zeolite with a pore diameter of between about 2.8 Å and about 4.2 Å, and in one example; the water selective adsorbent includes a zeolite with about 3 Å-4 Å pore diameter.

By one aspect, the water removal zone 10 includes a water removal device 11. In one approach, the water removal device includes a water removal vessel 12 as illustrated in FIG. 1 for holding the water selective adsorbent, such that the hydrocarbon feed stream enters the water removal vessel 12 through the inlet 15 to contact the water selective adsorbent and exits through the outlet 20. The inlet 15 and outlet 20 may be an inlet and outlet to the vessel 12. Alternatively the water removal zone 10 may be combined into a single vessel with one or both of the nitrogen removal zone 30 and the unsaturated aliphatic compound removal zone 50. Internal structures or equipment within a single vessel may separate the different zones. In this regard, the inlet and/or outlet may be an inlet and/or outlet to or from a particular region of a larger vessel that contains the water removal zone 10 and one or more of the other zones. According to other aspects, the water removal device 11 may include trays or a drier for removing a portion of the water from the hydrocarbon stream as is generally known in the art.

By one approach, as the hydrocarbon feed stream passes through the water removal zone, it enters the water removal vessel 12 and contacts the water selective adsorbent under contacting conditions, so that at least a portion of the water within the hydrocarbon feed stream is removed by the water selective adsorbent. In an example, the contacting temperature ranges from about 10° C. to about 300° C. and the contacting temperature may range from about 20° C. to about 250° C. In another example, the contacting temperature ranges from about 25° C. to about 225° C.; and the contacting temperature may range from about 50° C. to about 125° C.

In one example, at least about 50% of the water is removed from the hydrocarbon feed stream. In another example, between about 60% and about 99% of the water, and in yet another example between about 80% and about 99% of the water is removed from the hydrocarbon feed stream as it contacts the water selective molecular sieve. According to one aspect, the feed stream includes between about 10 and about 1000 ppm water. After the hydrocarbon feed stream passes through the water removal zone 10 and contacts the water selective adsorbent, the reduced water content feed stream includes between about 0.1 and about 100 ppm water. By another approach, after the hydrocarbon feed stream passes through the water removal zone 10, the reduced water content feed stream includes between about 0.1 and about 30 ppm water. By yet another approach, the reduced water content feed stream includes less than about 10 ppm water. By one aspect, the water selective adsorbent removes substantially all of the water in the feed stream, by one example above 95% of the water in the feed stream is removed. It should be noted that according to various aspects, it may be desirable that only a portion of the hydrocarbon feed stream may be contacted with the water removal adsorbent in the water removal zone 10 where not all of the water in the feed stream needs to be removed. In this regard, the remainder of the feed stream may bypass the water removal adsorbent or the water removal zone 10 entirely so that only a portion of the water is removed from the hydrocarbon feed stream. The bypass stream may then rejoin the treated stream.

In this manner, water is adsorbed by the water selective adsorbent, while a large portion of the nitrogen compounds and unsaturated aliphatic compounds in the hydrocarbon feed stream pass downstream through the outlet 20 and through line 25 for further treatment. In this manner, the water molecules which have been identified to quickly deactivate basic adsorbents that are useful for removing nitrogen compounds, are mostly removed from the hydrocarbon feed stream by the time it exits the outlet 20 and is passed downstream to the nitrogen removal zone 30 to reduce their poisoning of the nitrogen selective adsorbent.

By various aspects, as described previously, after the feed stream passes through the water removal zone 10 the reduced water feed stream is passed to the nitrogen removal zone 30, which removes at least a portion of one or more nitrogen compounds from the feed stream. As discussed above, various methods are well known in the art to remove nitrogen compounds from aromatic hydrocarbon streams. See, for example, U.S. Pat. Nos. 7,205,448; 7,744,828; 6,297,417; each of which is herein incorporated by reference in its entirety. In brief, the treated hydrocarbon stream is introduced to the nitrogen removal zone which includes at least one adsorbent effective to remove nitrogen. The nitrogen compounds may be removed from the hydrocarbon stream by various mechanisms such as adsorption, reaction, and reactive adsorption with the adsorbent. By one aspect, the nitrogen removal zone 30 may include a nitrogen selective adsorbent that preferentially adsorbs nitrogen over one or more other components in the feed stream. It should be understood, however, that the nitrogen selective adsorbent may also adsorb other components in the feed stream, such as, for example, water or one or more unsaturated aliphatic compounds from the feed stream. Further, in accordance with other aspects, other components may be provided in the nitrogen removal zone in addition to, or instead of, the nitrogen selective adsorbent for removing at least a portion of the nitrogen from the feed stream By one aspect, the nitrogen removal adsorbent may include an acidic adsorbent. In this regard, suitable adsorbents include acidic clays, resins, and zeolites. By one aspect, the nitrogen removal zone may comprise two adsorbents such as an acidic clay or resin adsorbent being located upstream of an acidic zeolite adsorbent so the treated hydrocarbon stream contacts the clay or resin adsorbent first to produce an intermediate stream which then contacts the zeolite adsorbent.

Suitable acidic zeolites for use in a nitrogen removal zone may include those having a high number of accessible sites that are able to interact with nitrogen containing molecules. Acidic zeolites suitable for removing nitrogen compounds in hydrocarbons includes but not limited to zeolites BPH, EMT, Faujasite, LTL, BEA, MAZ, MOR, MFI, MEI and mixtures thereof. The ranges of silica to alumina ratios depend on the specific structure of the zeolite used, but may typically range from about 2 to about 40. The choice of zeolites depends on the type and concentration of nitrogen compounds and the degree of nitrogen removal desired. In general, at least 50% of framework anion is balanced by proton and preferably at least 70% of the framework anion is balanced by proton.

It has been discovered that acidic zeolites, such as H—Y, currently used to adsorb nitrogen compounds may favor water adsorption to a much greater extent than nitrogen compounds. In this regard, significant adsorbent capacity may be taken up by water in the stream, shortening the cycle length of the adsorbent. Acidic zeolites may also catalyze the polymerization of dienes, leading to the blockage of accessible surface area and coking when the adsorbent is regenerated by carbon burn. By removing at least a portion of the water upstream in accordance with various aspects, some of these problems may be reduced.

By another aspect, the nitrogen selective adsorbent may include a preferred basic zeolite in order to decrease the extent of polymerization of dienes or other unsaturated aliphatic compounds within the stream. The basic zeolite used in the nitrogen removal zone 30, in accordance with various aspects, is less susceptible to deactivation by dienes than an acidic adsorbent, so that the hydrocarbon feed stream can be treated for nitrogen removal in nitrogen removal zone 30 in the presence of dienes in the stream without quickly deactivating the zeolite, increasing the amount of time between change-out or regeneration of the nitrogen selective adsorbent.

In this regard, the nitrogen selective adsorbent may include a basic zeolite for contacting the hydrocarbon feed stream and removing a nitrogen compound therefrom as is generally known in the art. According to one aspect, the nitrogen selective adsorbent may include a basic zeolite material, for example like those described in U.S. Pat. No. 5,271,835, which is incorporated by reference herein. The particular zeolite may be selected to have a high cation density of above about 50 in one example, between about 60 and about 99 in another example, and between about 80 and 99 in yet another example. By one aspect, the nitrogen selective adsorbent may include a zeolite having a silicon to aluminum ratio (Si/Al) of between about 1 and about 12. By another aspect, the nitrogen selective adsorbent may have a Si/Al ratio of between about 1.2 and 6.0. The nitrogen selective adsorbents according to this aspect may include zeolite LTA, BPH, EMT, Faujasite, LTL, MOR and the mixture of thereof, with at least 50% of framework charges balanced by alkali and/or alkali earth cations.

The nitrogen removal zone 30 may include a nitrogen removal vessel 32 as illustrated in FIG. 1 for holding the nitrogen selective adsorbent, such that the hydrocarbon feed stream enters the nitrogen removal vessel 32 through the inlet 35 to contact the nitrogen selective adsorbent and exit through the outlet 40. In this approach, the inlet 35 and outlet 40 may be an inlet and outlet to the vessel 32. The nitrogen removal zone 30 may also be combined into a single vessel with one or both of the water removal zone 10 and the unsaturated aliphatic compound removal zone 50. Internal structures or equipment within a single vessel may separate the different zones. In this regard, the inlet and/or outlet may be an inlet and/or outlet to or from a particular region of a larger vessel that contains the nitrogen removal zone 30 and one or more of the other zones.

By one aspect, as the hydrocarbon feed stream passes through the nitrogen removal zone 30, it contacts the nitrogen selective adsorbent under contacting conditions, so that at least a portion of one or more nitrogen compounds within the hydrocarbon feed stream is removed by the nitrogen selective adsorbent. In an example, the contacting temperature ranges from about 10° C. to about 300° C. and the contacting temperature may range from about 20° C. to about 125° C. In another example, the contacting temperature ranges from about 25° C. to about 90° C.

In one example, at least about 50% of the nitrogen is removed from the hydrocarbon feed stream, as measured, for example by a nitrogen chemiluminescence method, ASTM D4629. In another example, between about 70% and about 99.99% of the nitrogen is removed from the hydrocarbon feed stream as it contacts the nitrogen selective molecular sieve, and in another example between about 90% and about 99.99% of the nitrogen is removed. According to one aspect, the hydrocarbon feed stream to the nitrogen removal zone 30 includes between about 0.03 and about 10 ppm nitrogen.

By one aspect, where water is removed from the feed stream upstream of the nitrogen removal zone, the breakthrough time before nitrogen reaches detectable levels in an effluent stream generated by the nitrogen removal zone 30 is increased. In one example, the breakthrough time is at least about 10 hours. In another example, the breakthrough time is at least about 25 hours. In yet another example, the breakthrough time is at least about 50 hours. By another aspect, the nitrogen adsorption at breakthrough of the nitrogen removal adsorbent is above about 50% in one example, above about 75% in another example, and above about 80% in yet another example.

By another aspect, the feed stream entering the nitrogen removal zone includes at least one unsaturated aliphatic compound. However, it has been identified that by selecting a nitrogen removal adsorbent as discussed above, including a basic adsorbent according to one aspect, the presence of the aliphatic compound in the feed stream does not largely affect the adsorption performance or life of the nitrogen selective adsorbent. In one example, the feed stream entering the nitrogen removal zone 30 includes at least about 100 ppm-wt of unsaturated aliphatic compounds. In another example, the feed stream entering the nitrogen removal zone 30 includes between about 100 and about 3000 ppm-wt of unsaturated aliphatic compounds. In one example, the unsaturated aliphatic compound is a diene. In one example, the breakthrough time of the adsorbent where the feed stream includes at least about 100 ppm-wt of unsaturated aliphatic compounds in one example and at least about 400 ppm-wt of unsaturated aliphatic compounds in another example decreases by less than 15% in one example, by less than 10% in another example, and by less than 5% in yet another example, when compared to the breakthrough time of the same adsorbent where less than 1 ppm-wt of the unsaturated aliphatic compound is present in the feed stream. The adsorption of the nitrogen selective adsorbent at breakthrough decreases by less than 0.2% in one example, by less than 0.1% in another example, and by less than 0.05% in yet another example when compared to the adsorption at breakthrough of the same adsorbent where less than 1 ppm-wt of the unsaturated aliphatic compound is present in the feed.

In accordance with various aspects, the treatment zone 4 includes an unsaturated aliphatic compound removal zone 50 for removing or converting at least one unsaturated aliphatic compound from the hydrocarbon feed stream. The unsaturated aliphatic compound removal zone 50 may include an unsaturated aliphatic compound removal material that removes at least a portion of the unsaturated aliphatic compounds from the stream or reacts with the unsaturated aliphatic compounds to convert them into other compounds. By one aspect the unsaturated aliphatic compound removal material is an unsaturated aliphatic compound adsorbent that adsorbs at least one unsaturated aliphatic compound from the feed stream. By one aspect, the unsaturated aliphatic compound adsorbent adsorbs an unsaturated aliphatic compound in the feed stream but does not substantially adsorb an aromatic compound in the hydrocarbon feed stream.

Alternatively, according to various aspects, the unsaturated aliphatic compound removal material may include an unsaturated aliphatic compound catalyst that catalyzes an alkylation reaction in which one or more unsaturated aliphatic compounds react with aromatics in the feed stream to form one or more alkylaromatics. In this regard, the unsaturated aliphatic compound catalyst may include an acidic catalyst, which may include, but is not limited to acidic clay, acidic zeolite and sulfate supported metal oxides at a combination of temperatures and pressures under which the alkylation reaction operates in liquid or partial liquid phase conditions. For example, where the feed stream includes diolefins, the unsaturated aliphatic compound catalyst may catalyze an alkylation reaction of the diolefin. More particularly, benzene within the feed stream may alkylate the diolefin and add benzene to the double bond of the diolefin. In one example, the alkylation reaction forms an alkylbenzene, and may form diphenylbenzene.

According to various aspects, the unsaturated aliphatic compound removal material may act as both an adsorbent and a catalyst such that a portion of the unsaturated aliphatic compound in the stream are removed by adsorption while another portion of the unsaturated aliphatic compound in the stream are reacted with aromatics in the stream by contacting the unsaturated aliphatic compound removal material to form one or more alkylaromatics.

By one aspect, the unsaturated aliphatic compound removal material includes clay and may include acidified clay. Suitable clays include, but are not limited to, beidellite, hectorite, laponite, montmorillonite, nontonite, saponite, bentonite, and mixtures thereof. In one form, the clay adsorbent includes an acid activated bentonite and/or montmorillonite clay.

Advantageously, by one aspect, in removing nitrogen compounds from the feed stream before it enters the unsaturated aliphatic compound removal zone, nitrogen does not poison the unsaturated aliphatic compound removal material, so that the life of the material is extended before requiring change-out or regeneration.

The hydrocarbon feed stream to be treated is contacted with the unsaturated aliphatic removal material at contacting conditions to remove or react one or more unsaturated aliphatic compounds and produce a hydrocarbon stream with a reduced unsaturated aliphatic compound concentration relative to the hydrocarbon feed stream entering the inlet 55 of the unsaturated aliphatic compound removal zone 50. The unsaturated aliphatic compounds may be removed from the hydrocarbon stream by various mechanisms such as adsorption, reaction, and reactive adsorption with the adsorbent. The treated hydrocarbon stream has a lower unsaturated aliphatic compound concentration relative to the unsaturated aliphatic compound content of the hydrocarbon feed stream.

The unsaturated aliphatic compound removal zone 50 may include an unsaturated aliphatic compound removal vessel 52 as illustrated in FIG. 1 for holding the unsaturated aliphatic compound removal material, such that the hydrocarbon feed stream enters the unsaturated aliphatic compound removal vessel 52 through the inlet 55 to contact the unsaturated aliphatic compound removal material and exit through the outlet 60. The inlet 55 and outlet 60 may be an inlet and outlet to and from the vessel 52. The unsaturated aliphatic compound removal zone 50 may also be combined into a single vessel with one or both of the water removal zone 10 and the nitrogen removal zone 30. Internal structures or equipment within a single vessel may separate the different zones. In this regard, the inlet and/or outlet 55 and 60 may be an inlet and/or outlet to or from a particular region of a larger vessel that contains the nitrogen removal zone 30 and one or more of the other zones.

The contacting conditions in one example include a temperature of at least about 50° C. In another example, the contacting temperature ranges from about 50° C. to about 300° C. In yet another example, the contacting temperature ranges from about 75° C. to about 250° C.

Bromine Index is commonly used to assess the unsaturated aliphatic compound content, including olefins and diolefins, of hydrocarbon mixtures. (It should be noted that the terms "diolefins" and "dienes" are used interchangeably herein) In one example, the unsaturated aliphatic compound removal zone 50 reduces the diolefin concentration in the hydrocarbon feed stream such that Bromine Index is reduced by at least 50%. The Bromine Index is reduced by at least about 70% in another example; at least about 90% in another example, and at least about 95 wt % in yet another example. As used herein the Bromine Index of the hydrocarbon streams or mixtures is determined using method UOP304. Unless otherwise noted, the analytical methods used herein such as UOP304 are available from ASTM International, 100 Barr Harbor Drive, West Conshohocken, Pa., USA.

Figure 2:
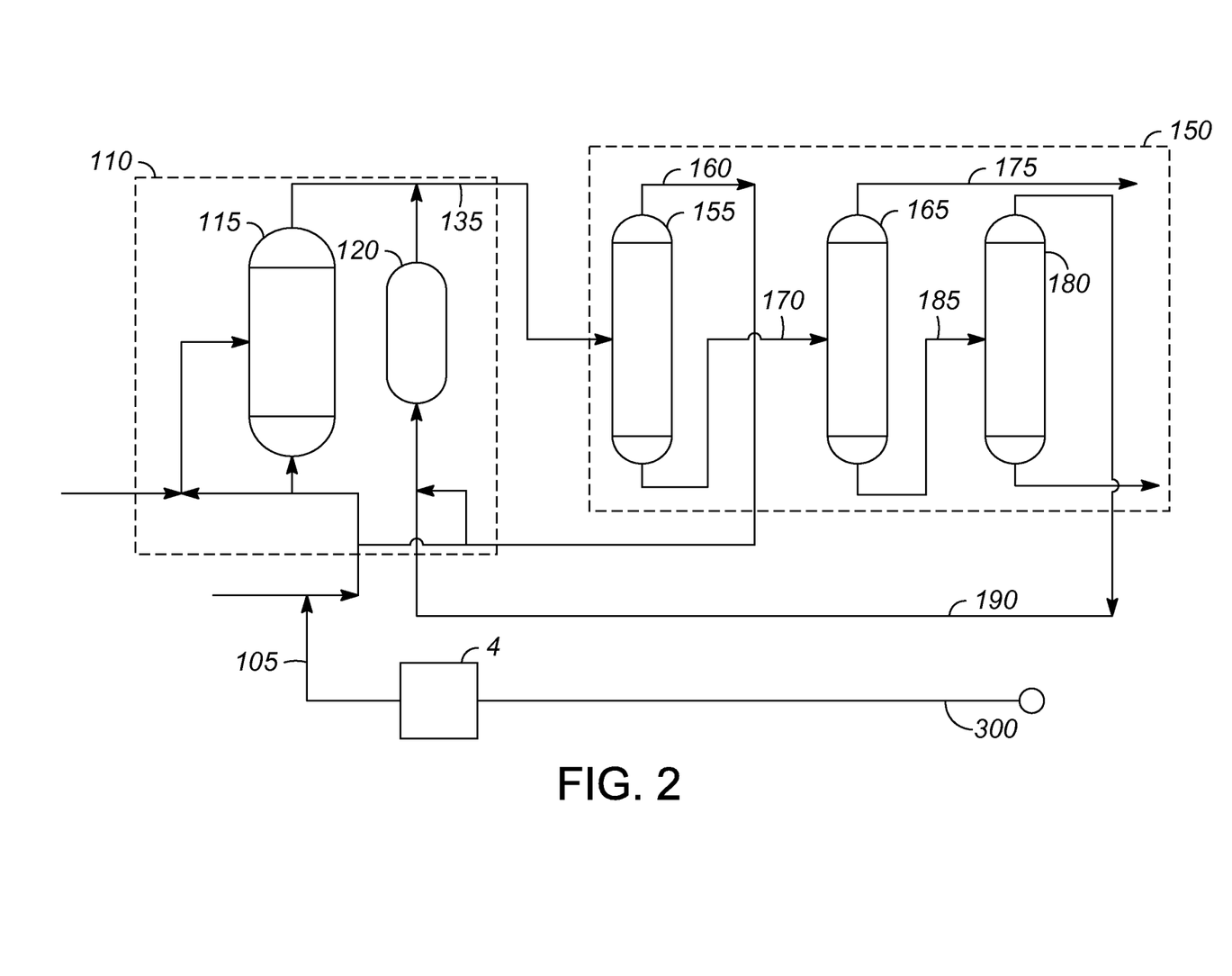
FIG. 2 is a flow diagram of an alkylation facility that includes a hydrocarbon feed stream treatment zone in accordance with various embodiments.

Turning to FIG. 2, by one aspect, the hydrocarbon stream treatment zone 4 is provided for treating a benzene feed stream to an alkylation zone 110. According to various aspects, the feed stream includes benzene, water, a nitrogen compound, and an unsaturated aliphatic compound as mentioned previously. After the benzene containing feed stream is treated in the hydrocarbon treatment zone 4 to remove at least a portion of water, a nitrogen compound, and an unsaturated aliphatic compound as described above with regard to FIG. 1, the treated feed stream is passed along conduit or line 105 to the alkylation zone 110. By one aspect, FIG. 2 illustrates that the alkylation zone 110 includes both an alkylation reactor 115 and a transalkylation reactor 120. However, the alkylation zone 110 may not include either the alkylation reactor 115 or the transalkylation reactor 120 and may include more than one alkylation reactor 115 and/or transalkylation reactor 120. FIG. 2 illustrates that the treated hydrocarbon feed stream is combined with another feed stream and passed into the alkylation reactor 115. However, it should be understood that the treated hydrocarbon feed stream can be combined with one or more other streams to pass into the alkylation reactor 115 or the transalkylation reactor 120 or be passed directly into the alkylation reactor 115 or transalkylation reactor 120.

In one aspect, the treated hydrocarbon stream is passed via line 105 to one or both of the alkylation reactor 115 and transalkylation reactor 120. Another feed stream 125 may be introduced to the alkylation zone 110 and combined with the treated hydrocarbon feed stream or passed separately to one or both of the alkylation reactor 115 and/or transalkylation reactor 120. In addition, or alternatively, one or more additional streams may be passed to the alkylation zone 110. An alkylating agent may be introduced into an alkylation reactor 115 and contacted with the treated hydrocarbon stream and an alkylation catalyst to produce an alkylated benzene product which is sent downstream via line 135. For example, ethylene may be introduced through line 130 to the alkylation reactor 115 to contact the alkylation catalyst in the presence of a treated benzene feed stream to produce an ethylbenzene stream.

In the alkylation of an aromatics alkylation substrate by an olefinic alkylating agent as catalyzed by an acidic catalyst, the olefins may contain from 2 up to at least 20 carbon atoms, and may be branched or linear olefins, either terminal or internal olefins. Thus, the specific nature of the olefin is not particularly important. Among the lower olefins, ethylene and propylene are the most important representatives. An olefinic feed stream may be introduced via line 130 and may include for example an alkylating agent of ethylene and/or propylene. Alkylating agents may also be provided by alkyl constituents of a polyalkylbenzene in a transalkylation reactor 120. Diethylbenzene, triethylbenzene and diisopropylbenzene are prominent examples of polyalkylbenzenes that can provide such alkylating agents.

A wide variety of catalysts can be used in the alkylation zone 110. Catalysts have typically included those that do not suffer deleterious effects from the presence of water. In one approach, a substantial quantity of water may be tolerated or desired in the presence of the alkylation catalyst. However, according to various aspects, other catalysts that are not as water tolerant may be used since at least a portion of the water in the hydrocarbon feed stream may be removed in the water removal zone 10 as discussed previously. The preferred catalyst for use in this invention is a zeolitic catalyst. The catalyst of this invention will usually be used in combination with a refractory inorganic oxide binder. Preferred binders are alumina or silica. Suitable zeolites include zeolite beta described in U.S. Pat. No. 5,723,710, ZSM-5, PSH-3, MCM-22, MCM-36, MCM-49, MCM-56, type Y zeolite, and UZM-8, which includes the aluminosilicate and substituted aluminosilicate zeolites described in U.S. Pat. No. 6,756,030 and the modified UZM-8 zeolites, such as, UZM-8HS which are described in U.S. Pat. No. 7,091,390. Each of U.S. Pat. Nos. 6,756,030 and 7,091,390 is herein incorporated by reference in its entirety.

The basic configuration of a catalytic aromatic alkylation zone is known in the art. The feed aromatic alkylation substrate and the feed olefin alkylating agent are preheated and charged to generally from one to four reactors in series. Suitable cooling means may be provided between reactors to compensate for the net exothermic heat of reaction in each of the reactors. Suitable means may be provided upstream of or with each reactor to charge additional feed aromatic, feed olefin, or other streams (e.g., effluent of a reactor, or a stream containing one or more polyalkylbenzenes) to any reactor in the alkylation zone. Each alkylation reactor 115 may contain one or more alkylation catalyst beds. The invention encompasses dual zone aromatic alkylation processes such as those as described in U.S. Pat. No. 7,420,098 which is herein incorporated by reference in its entirety.

The particular conditions under which the alkylation reaction is conducted depends upon the aromatic compound and the olefin used. One condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. The alkylation conditions usually include a pressure in the range between about 1379 kPa(g) and 6985 kPa(g). The alkylation of the aromatic compounds with the olefins in the C2 to C20 range can be carried out at a temperature of about 60° C. to about 400° C. In a continuous process this time can vary considerably, but is usually from about 0.1 to about 8 $hr^{-1}$ weight hourly space velocity (WHSV) with respect to the olefin. In particular, the alkylation of benzene with ethylene can be carried out at temperatures of about 150° C. to about 260° C. and the alkylation of benzene with propylene at a temperature of about 90° C. to about 200° C. The ratio of alkylatable aromatic compound to olefin used in the instant process will depend upon the degree of monoalkylation desired as well as the relative costs of the aromatic and olefinic components of the reaction mixture. For alkylation of benzene by propylene, the benzene-to-olefin molar ratio may be as low as about 0.1 and as high as about 10. Where benzene is alkylated with ethylene a benzene-to-olefin ratio may be between about 0.1 and 10.

The alkylation reaction zone will often provide a wide variety of secondary by-products. For example, in the alkylation of benzene with ethylene to produce ethylbenzene, the reaction zone can also produce di- and triethylbenzene in addition to other ethylene condensation products. Another non-limiting exemplary reaction that is contemplated herein includes the alkylation of benzene with propylene to produce cumene. In this type of reaction, the reaction zone can produce di- and triisopropylbenzene in addition to still more condensation products. As is well known in the art, these polyalkylated aromatics may contact additional aromatic substrate in a transalkylation zone to produce additional monoalkylated product. See e.g. U.S. Pat. Nos. 7,622,622 and 7,268,267, which are incorporated by reference herein. It should be noted that transalkylation reactions may occur in an alkylation reaction zone and alkylation reactions occur in a transalkylation reaction zone. Thus, as used herein alkylation zone 110 refers to a zone in which one or both of alkylation and transalkylation reactions occur. In an embodiment, the alkylated benzene product comprises at least one of ethylbenzene and cumene.

An alkylated aromatic separation zone may also be provided for separating a concentrated alkylated aromatic stream from the alkylated aromatic stream produced by the alkylation zone 110. The alkylated aromatic separation zone may include one or more distillation or fractionation columns or other separation apparatus as known in the art for separating a concentrated alkylated aromatic stream from other components in the alkylated aromatic stream. I should be noted that the term "concentrated" as used herein does not mean the resultant stream is free from other components, but rather that it has a higher concentration of the desired product than the stream fed into the separation apparatus. For example, as illustrated in FIG. 2, where the alkylation zone produces an ethylbenzene stream via line 135, the alkylated aromatic separation zone may include an ethylbenzene separation zone 150 for separating a concentrated ethylbenzene stream from a stream including benzene, poly-ethylbenzene, and other components. A benzene fractionation column 155 may be in fluid communication with an outlet of the alkylation zone 110 and configured to receive the ethylbenzene stream via line 135 from the alkylation zone outlet and to separate benzene from the feed stream, which exits the benzene fractionation column through an alkylation benzene recycle stream via line 160. The alkylation benzene recycle stream may be passed back to the alkylation zone 110 as additional benzene feed. An ethylbenzene fractionation column 165 may be in fluid communication with the benzene fractionation column 155 via line 170 and may be provided to receive the benzene reduced ethylbenzene stream via line 170 to produce a concentrated ethylbenzene stream via fractionation. The ethylbenzene may provide a product stream or it may be transferred downstream via line 175. A poly-ethylbenzene fractionation column 180 may be provided to receive the ethylbenzene depleted stream via line 185 and to separate a concentrated poly-ethylbenzene stream, which may be recycled back to a transalkylation reactor 120 via line 190 as a feed to the transalkylation reactor to produce additional ethylbenzene.

Figure 3:
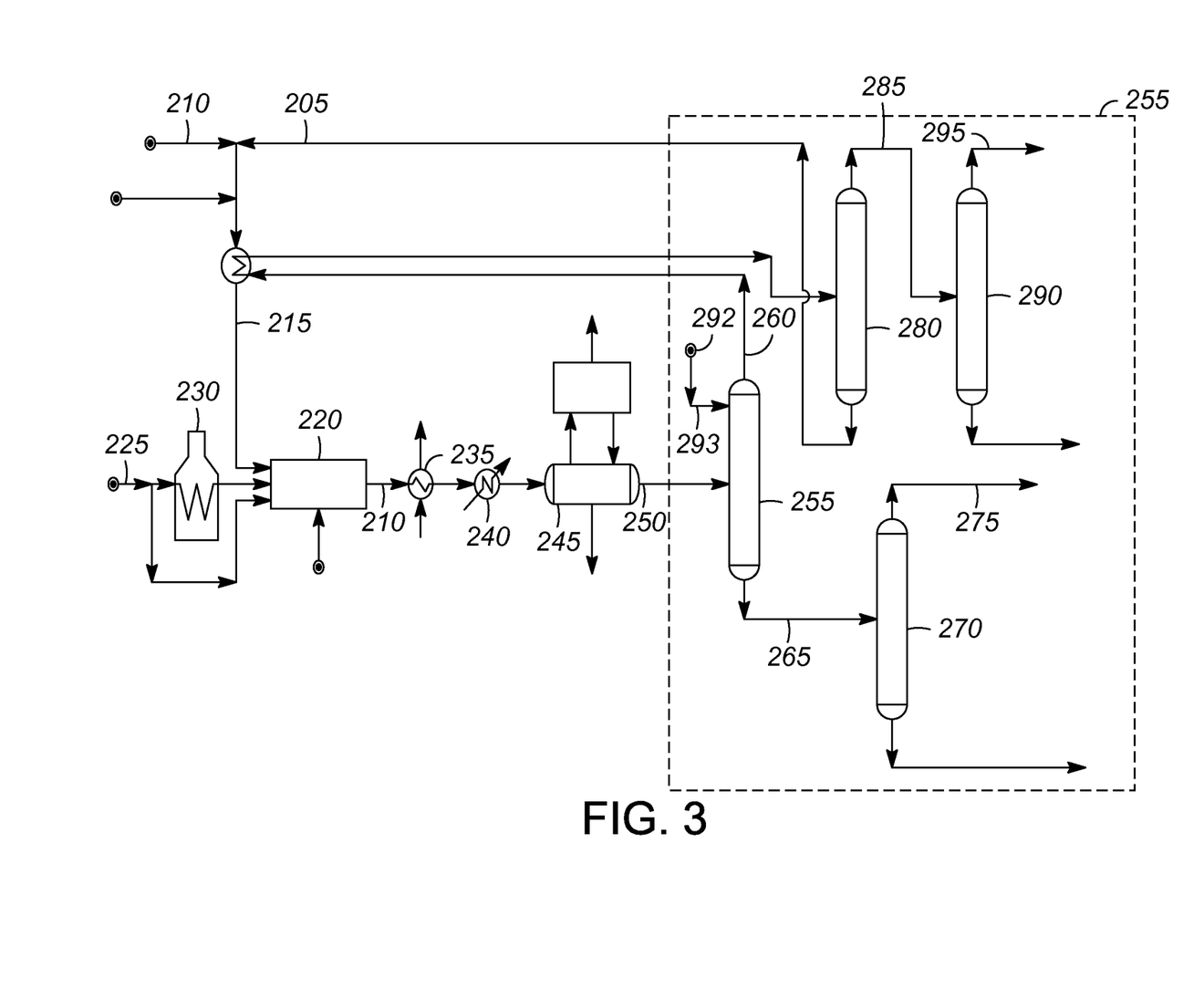
FIG. 3 is a flow diagram of a styrene monomer facility in accordance with various embodiments.

According to an aspect, the hydrocarbon stream may include a benzene recycle stream provided from a styrene monomer production zone. Turning to FIG. 3, an example of a styrene production zone 205 of a styrene production plant is illustrated. An ethylbenzene feed stream may be provided to the styrene monomer production zone 205 via line 210. The ethylbenzene feed stream may be provided via line 210 by forming the ethylbenzene stream by alkylation in the alkylation zone 110 and separation of the alkylation zone ethylbenzene stream by the separation zone 150 via line 175 to provide a concentrated ethylbenzene stream, which may include one or more other components, including benzene, as described above with regard to FIG. 2, or it may be provided by another source. In the styrene monomer production zone 205, the ethylbenzene stream is passed to a dehydrogenation zone 220 via line 215, where a dehydrogenation reaction occurs to produce a styrene stream via line 215.

The general layout and operation of styrene monomer production plants is well known, and one process flow is described and shown generally in U.S. Pat. No. 4,479,025, which is incorporated by reference herein. In an exemplary system, the dehydrogenation zone 220 includes one or more dehydrogenation reactors with a dehydrogenation catalyst for contacting the ethylbenzene stream and converting a portion of the ethylbenzene to styrene to form a mixed styrene stream, as is generally known in the art. The dehydrogenation zone 220 may also include steam sources and/or generators 225 and a superheater 230 for heating the steam, which is combined with the ethylbenzene feed stream and passed to the dehydrogenation zone 220. In the dehydrogenation zone 220, the ethylbenzene in the stream is contacted with the dehydrogenation catalyst under dehydrogenation conditions to produce a stream that includes unreacted ethylbenzene, styrene, benzene, toluene, steam, and hydrogen. The mixed styrene stream is cooled via heat exchanger 235 and sent to condenser 240 to produce a mixed phase stream. The stream is separated in the mixed phase separator into a liquid phase including water with dissolved hydrocarbons, a vapor phase, and a hydrocarbon liquid phase. The hydrocarbon liquid phase stream may include styrene, ethylbenzene, toluene, benzene, and other components, and is passed via line 250 to a separation zone 255.

As illustrated in FIG. 3, the separation zone may include an ethylbenzene/styrene splitter 255 for separating an ethylbenzene stream, including benzene and toluene, via line 260 from a styrene concentrated stream via line 265. The concentrated styrene stream may be passed via line 265 to a styrene finishing column 270 to produce a styrene product via line 275. The ethylbenzene stream may be passed via line 260 to an ethylbenzene recycle column 280. The ethylbenzene recycle column separates an ethylbenzene recycle stream and a stream including lighter hydrocarbon components, including benzene, which is passed via line 285 to benzene column 290. The benzene column 290 separates a benzene recycle stream that is exits the benzene column 290 via line 295.

According to one aspect, an inhibitor is added to the hydrocarbon liquid phase stream as is generally known in the art, in order to restrict the styrene from polymerizing and/or causing corrosion of the separation equipment. As described previously, the inhibitor may include one or more nitrogen compounds generally known to restrict polymerization of styrene and/or corrosion of equipment. Potential inhibitors are described above. As illustrated in FIG. 3. the inhibitor may be introduced from an inhibitor source 292 into the ethylbenzene/styrene splitter 255 via line 293.

Referring back to FIG. 2, the benzene recycle stream may be passed via line 300 back to the alkylation zone 110 for alkylation of the benzene stream in the presence of ethylene to form additional ethylbenzene. Due to the introduction of the inhibitor and steam during the dehydrogenation and separation processes in the styrene monomer production zone 205 described previously with regard to FIG. 3, the recycle benzene stream will typically include water, one or more nitrogen containing compounds, and one or more unsaturated aliphatic compounds as described above. In this regard, the benzene recycle stream may be passed via line 300 to the hydrocarbon treatment zone 4 described previously with regard to FIGS. 1 and 2, to remove at least a portion of these components prior to the benzene recycle stream entering the alkylation zone 110, where these components could potentially cause deactivation of the alkylation or transalkylation catalyst or otherwise shorten the life of the catalyst.

The exemplary ethylbenzene production plant and styrene monomer production plant illustrated in FIGS. 2 and 3 respectively are intended to illustrate one possible process flow, and are not intended to limit the scope of the invention which may be practiced in other process flows.

By one aspect, a method is provided for treating a hydrocarbon feed stream including an aromatic compound, a nitrogen compound, an unsaturated aliphatic compound, and water as described previously. The method includes removing at least a portion of the water from the hydrocarbon feed stream. By one aspect, the method includes contacting the hydrocarbon stream with a water selective adsorbent at contacting conditions to remove the water from the feed stream. The method further includes contacting the hydrocarbon stream with a nitrogen selective adsorbent at contacting conditions to remove a nitrogen compound from the feed stream. The method also includes contacting the hydrocarbon stream with an unsaturated aliphatic compound removal material to remove an unsaturated aliphatic compound from the hydrocarbon stream to produce a treated hydrocarbon stream. The method according to this aspect may include contacting the hydrocarbon stream with an unsaturated aliphatic compound adsorbent, an unsaturated aliphatic compound catalyst, or both.

By one aspect, the above steps are carried out sequentially. It has been found that by contacting the hydrocarbon feed stream with particular adsorbents and/or materials as described previously, in this order, the contaminants can be removed from the hydrocarbon feed stream so that it can provide a useful feed to an alkylation zone without deactivating the alkylation and/or transalkylation catalysts. Surprisingly, it has also been identified, that the selection of particular adsorbent and/or catalyst materials, and the order of contacting the hydrocarbon stream with the adsorbents, removes compounds from the feed stream that can reduce the life of the downstream adsorbents. Namely, by first removing water from the feed stream, for example by first contacting the hydrocarbon feed stream with a water selective adsorbent, at least a portion of water is removed from the feed stream so that the water is not substantially shorten the lifecycle of the nitrogen selective adsorbent and/or the unsaturated aliphatic compound removal material. By next contacting the hydrocarbon feed stream with a nitrogen selective adsorbent, at least a portion of the nitrogen compounds are next removed from the hydrocarbon feed stream so that these nitrogen compounds do not as quickly deactivate the unsaturated aliphatic compound removal material. This can increase the amount of time that the process may proceed before these downstream adsorbents and/or catalysts must be changed-out or regenerated.

The above description and examples are intended to be illustrative of the invention without limiting its scope. While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

EXAMPLE 1

For each test, a basic zeolitic adsorbent for removing nitrogen compounds from a feed stream included a commercially available 13X-HP adsorbent. Prior to each test, the adsorbent was pre-dried at 550° F. for 4 hours in flowing nitrogen.

EXAMPLE 2

For Examples 3 and 4, 18.21 g of 8×14 mesh 13X-HP beads were loaded into the isothermal zone of a ⅝" diameter reactor. The reactor was kept at a constant temperature of 40° C. and pure benzene was flowed through the reactor at 90 g/hr to pressurize the system up to 550 psig. Once the system reached 550 psig, feed was introduced at 90 g/hr and the reactor effluent was analyzed via gas chromatography.

Two different samples of a commercial benzene recycle stream (>99 wt % benzene) containing different amounts of one or more of nitrogen compounds and dienes were used to evaluate the effectiveness of the 13X-HP adsorbent to remove the nitrogen compounds as described below. The analysis of the two example feeds is reported in Table 1 with the analysis of the effluent or product from each test. The nitrogen compound content was determined by gas chromatography.

EXAMPLE 3

As an illustrative example, a benzene feed stream sample containing 60 wt-ppm acetonitrile was used in the test according to Example 1. The feed stream according to Example 2 had a dew point of −40 C and a dienes level of 1000 wt-ppm.

EXAMPLE 4

As an illustrative example, a benzene feed stream (>99 wt-% benzene) sample containing 66 wt-ppm Acetonitrile and 904 wt-ppm Isoprene was used in the test according to Example 1 to determine the effect that the diene isoprene has on the performance of the 13X-HP. The feed stream according to Example 2 had a dew point of −40 C.

TABLE 1

| Example | Adsorbent | Feed | Feed Rate (K/hr) | Temperature (° C.) | Breakthrough (hours) | Nitrogen Ads. @ Breakthrough |
|---|---|---|---|---|---|---|
| 3 | LR-13X | 60 wt-ppm Acetonitrile | 90 | 40 | 77 | 0.859% |
| 4 | LR-13X | 904 wt-ppm Isoprene 66 wt-ppm Acetonitrile | 90 | 40 | ACN - 74 ISO - 6 | 0.826% |

EXAMPLE 5

In an illustrative example, a 400 ml solution of acetonitrile in benzene was prepared by adding acetonitrile and benzene to a 500 mL beaker. Acetonitrile was added to the solution at a concentration of 161 ppm by weight, or equivalently 55 ppmw nitrogen. Next, 0.96 grams of activated 13X-HP adsorbent was added to the beaker. A chemiluminescence analysis was performed by ASTM method D4629 to verify the initial concentration of acetonitrile. The beaker was then sealed and shaken for four hours. The chemiluminescence analysis was repeated to determine the amount of nitrogen present after shaking, and the amount of nitrogen adsorbed by the 13X-HP. The results are shown below in Table 2.

EXAMPLE 6

In a comparative example, 400 ml of a solution of acetonitrile, benzene, and water was prepared by adding acetonitrile, water, and benzene to a 500 mL beaker. Acetonitrile was added to the solution at a concentration of 161 ppm by weight, or equivalently 55 ppmw of nitrogen. In addition, 168.8 μL of water (501 ppmw) was added to the solution. Next, 1.00 grams of activated 13X-HP adsorbent was added to the beaker. A chemiluminescence analysis was performed by ASTM method D4629 to determine the initial concentration of acetonitrile in the solution. The beaker was then sealed and shaken for four hours. The chemiluminescence analysis was repeated to determine the amount of nitrogen present after shaking. The results are shown below in Table 2.

TABLE 2

| Example | Adsorbent | Solution | Nitrogen in Solution Before Shaking (wt-ppm) | Nitrogen in Solution After Shaking (wt-ppm) | Nitrogen on Adsorbent |
|---|---|---|---|---|---|
| 5 | LR-13X | 161 ppmw Acetonitrile in Benzene | 55 wt-ppm | 38 wt-ppm | 0.60 wt-% |
| 6 | LR-13X | 161 ppmw Acetonitrile 501 ppmw water in Benzene | 55 wt-ppm | 48 wt-ppm | 0.24 wt-% |

The invention claimed is:

1. A method for treating a hydrocarbon stream comprising benzene, a nitrogen compound, an unsaturated aliphatic compound, and water, the method comprising:
   a) contacting the hydrocarbon stream with a water selective adsorbent comprising a zeolite selected from the group consisting of zeolite A, zeolite X, and zeolite Y to remove at least a portion of the water from the hydrocarbon stream to form a stream reduced with water;
   b) contacting the stream reduced with water from step (a) with a nitrogen selective adsorbent comprising a basic zeolite at contacting conditions to remove said nitrogen compound from the stream of step (a) to form a stream reduced with nitrogen compound;
   c) contacting the stream reduced with nitrogen compound of from step (b) with an unsaturated aliphatic compound removal material to remove an unsaturated aliphatic compound from the hydrocarbon stream to produce a treated hydrocarbon stream;
   d) contacting the treated hydrocarbon stream with an alkylation catalyst and ethylene under alkylation conditions to convert at least a portion of the benzene to ethylbenzene to form an ethylbenzene hydrocarbon stream;
   e) contacting the ethylbenzene hydrocarbon stream including ethylbenzene with a dehydrogenation catalyst under dehydrogenation conditions to convert at least a portion of the ethylbenzene to styrene to form a styrene stream;
   separating a benzene recycle stream from the styrene stream; and
   introducing the benzene recycle stream as at least a portion of the hydrocarbon stream for treating thereof according to steps a-c.

2. The method of claim 1, wherein the unsaturated aliphatic compound removal material comprises an unsaturated aliphatic compound catalyst.

3. The method of claim 1, wherein the unsaturated aliphatic compound removal material comprises an unsaturated aliphatic compound adsorbent.

4. The method of claim 1, wherein the zeolite has a pore diameter of between about 2 Å and 5 Å and comprises Zeolite A.

5. The method of claim 1, wherein the zeolite has a pore diameter of between about 5 Å and 8 Å, and comprises Faujasite.

6. The method of claim 1, wherein the nitrogen selective adsorbent includes a basic zeolite where more than 90% of the cations are alkali or alkaline earth elements.

7. The method of claim 1, wherein the basic zeolite has a Si/Al ratio of between about 1 and about 12.

8. The process of claim 1, wherein the unsaturated aliphatic compound comprises a diene and the unsaturated aliphatic removal material comprises a material selected from the group consisting of acidic clay, acidic zeolite and sulfate supported metal oxides.

* * * * *